(12) United States Patent
Hescheler

(10) Patent No.: US 7,105,344 B2
(45) Date of Patent: Sep. 12, 2006

US007105344B2

(54) FLUORESCENT PROTEINS AS CELL-TYPE SPECIFIC REPORTERS

(75) Inventor: Jürgen Hescheler, Köln (DE)

(73) Assignee: Axiogenesis AG, (DE)

( * ) Notice: Subject to any disclaimer, the term of this patent is extended or adjusted under 35 U.S.C. 154(b) by 284 days.

(21) Appl. No.: 10/084,960

(22) Filed: Feb. 28, 2002

(65) Prior Publication Data

US 2002/0092035 A1 Jul. 11, 2002

Related U.S. Application Data

(63) Continuation of application No. 09/446,717, filed as application No. PCT/EP98/03988 on Jun. 30, 1998.

(30) Foreign Application Priority Data

Jul. 2, 1997 (DE) .................................. 197 27 962

(51) Int. Cl.
*C12N 5/00* (2006.01)
*C07H 21/02* (2006.01)
*C07H 21/04* (2006.01)

(52) U.S. Cl. ..................... 435/325; 536/23.1; 536/23.4

(58) Field of Classification Search .................... 800/21
See application file for complete search history.

(56) References Cited

FOREIGN PATENT DOCUMENTS

WO    WO 98/36081    8/1998

OTHER PUBLICATIONS

Va Maltsev et al., Circ Res., "Cardiomyocytes Differentiated In Vitro from Embryonic Stem Cells Developmentally Express Cardiac-Specific Genes and Ionic Currents," 1994, 75:233-244.
J Rohwedel et al., Developmental Biology, "Muscle Cell Differentiation of Embryonic Stem Cells . . . Myogenic Determination Genes and Functional Expression of Ionic Currents," 1994, 164:87-101.
E. Koslossov et al. "Functional Characteristics of ES Cell-derived Precursor Cells Identified by Tissue-specific Expression of the GreenFluorescent Protein", Journal of Cell Biology, vol. 143, No. 7, Dec. 1998, pp. 2045-2056.
Gail R. Martin et al., "Differentiation of Clonal Lines of Teratocarcinoma Cells: Formation of Embryoid Bodies *In Vitro*", Proc. Natl. Acad. Sci. USA, vol. 72, No. 4, Apr. 1975, pp. 1441-1445.
Weei-Yuarn Huang et al., "Transgenic expression of green fluorescence protein can cause dilated cardiomyopathy", Nature Medicine, vol. 6, No. 5, May 2000, pp. 482-484.
P. Delabesse et al., "Green Fluorescent Protein (GFP) Gene Transfer Into Hematopoietic Cell Lines and ES Cells", Blood vol. 88, No. 10, Suppl. 1, part 1-2, 1996, p. 295b.
Ikawa et al. Development Growth and Differentiation 37:455-459 (Aug. 1995).
Wobus et al. Roux's Archives of Developmental biology 204:36-45 ( Oct. 1994).
Wobus et al. Circulation 92(8) -Supplement 1 (Oct. 1995).
Heim et al. Current Biology 6(2):178-82 (Feb. 1996).
Malstev et al. Circulation Research 75(2):233-44 (Aug. 1994).
Chen et al. Journal of Biological Chemistry 270(26):15628-33 (Jun. 1995).
Hammer et al. Journal of Animal Science 63: 269-278 (Jul. 1986).
Wall et al. Journal of Diary Science 80:2213-24 (1997).
Mullins et al. Journal of Clinical Investigation 97(7): 1557-1560 (1996).
Moreadith et al. Journal of Molecular Medicine 75:208-216 (1997).
Seamark, RF Reprod. Fertil. Dev. 6:653-7 (Feb. 1995).
Nichols et al. Development 110:1341-1348 (1990).
Piedrahita et al. Threiogenolgy 34(5):879-901 (Nov. 1990).
Zernicka-Goetz et al. Development 124:1133-1137 (Mar. 1997).
Li Y et al. "Use of a Green Fluorescent Protein in Studies of Apoptosis of Transfected Cells" Biotechniques, Bd. 23, Nr. 6, 1997, Seiten 1026-1029, XP002968179 siehe Seite 1027, letter Abstatz.

*Primary Examiner*—Joseph T. Woitach
(74) *Attorney, Agent, or Firm*—Medlen & Carroll, LLP

(57) ABSTRACT

The present invention related to non-human mammal embryonic stem (ES) cells stably transfected with a DNA construct comprising a DNA sequence coding for a non-cell damaging fluorescent protein and a cell- and/or development-dependent promoter operably linked with said DNA sequence; a method for preparing such ES cells; a cell culture obtainable by culturing said ES cells; a method for the toxicological examination of substances using such cell cultures; a method for producing transgenic non-human mammals using said ES cells; a transgenic non-human mammal obtainable by said method; and a method for examining stages of cellular development using cells of such a non-human mammal.

3 Claims, 4 Drawing Sheets

FLUORESCENT PROTEINS AS CELL-TYPE SPECIFIC REPORTERS

This application is a continuation of U.S. Ser. No. 09/446,717, filed on Apr. 13, 2000, now pending, which is, in turn, a 371 of PCT/EP98/03988, filed on Jun. 30, 1998. Priority of both applications is claimed.

The present invention relates to the use of non-cell-damaging fluorescent proteins as cell-type specific reporters. In detail, the invention relates to non-human mammal embryonic stem (ES) cells stably transfected with a DNA construct comprising a DNA sequence coding for a non-cell-damaging fluorescent protein and a cell- and/or development-dependent promoter operably linked with said DNA sequence; a method for preparing such ES cells; a cell culture obtainable by culturing said ES cells; a method for the toxicological examination of substances using such cell cultures; a method for producing transgenic non-human mammals using said ES cells; a transgenic non-human mammal obtainable by said method; and a method for examining stages of cellular development using cells of such a non-human mammal.

Embryonic stem (ES) cells both are the basis of the creation of transgenic animal models and can be used for in vitro cell culture systems. To date, the cell types differentiating from ES cells have been identified by characterizing them by antibody staining or by in situ hybridization with antisense oligonucleotides. However, to do this, the cells had to be fixed first. None of the prior art methods are suitable for subsequent functional studies with the different cell types differentiated from ES cells. To date, the only method for performing functional studies on ES-cell derivatives in vivo has been morphological identification. It has been successful, although very unsatisfactorily, with cardiac and skeletal muscle cells because they were characterized by contractions. Already with the non-contracting ventricular cells, recognition for functional studies was difficult. Thus, in Maltsev et al., 1994, Circ. Res., 75, 233–244, and DD-299439 A5, a model is described in which the differentiation of heart cells (cardiomyocytes) takes place in vitro from a very early stage of development to a specialized pacemaker, ventricular or atrial heart cell (Maltsev et al., 1994, Circ. Res., 75, 233–244). For this purpose, totipotent embryonic stem (ES) cells of cell line D3 are differentiated into cardiomyocytes under the following cell culture conditions: The cells are placed in a hanging drop for 2 days, then kept in suspension for 5 days and subsequently plated (Maltsev et al., 1994, Circ. Res., 75, 233–244). Within 1–2 days from the plating, beating areas spontaneously form within these "embryoid bodies" (EBs). From these areas, individual cardiomyocytes can be dissociated using enzymatic digestion (collagenase); these cardiomyocytes are accessible to functional, molecular-biological and morphological (immune histochemistry, electron microscopy) examination techniques during the various differentiation stages. In addition to cardiomyocytes, the thus generated EBs also include, inter alia, neurons, glia cells, hematopoietic cells, endothelial cells (early capillary), smooth muscle cells, skeletal muscle cells, cartilage cells, fibroblasts and epithelial cells.

In addition, bioluminescent proteins such as Green Fluorescent Protein (GFP hereinafter) have recently been described (Prasher et al., Gene, Vol. 111, 229–233 (1992)); they are proposed for use as markers in gene expression (Chaffie et al., Science, Vol. 263, 802–805 (1994)). Thus, WO-A-95/07463 and WO-A-96/2767S disclose the transformation of cells with GFP. However, the transformation of mammal cells, especially mammal ES cells, with a DNA sequence coding for GFP has been described neither in this nor in another reference.

Cardiovascular diseases are still among the most frequent causes of death in the Western industrial countries. Only through intensive basic research in this field, the pathophysiological causes can be found, and new therapeutic approaches can be devised, and toxicological changes described. For studying the pathogenesis of cardiovascular diseases and for testing new pharmacological and toxicological substances, models are needed which, on one hand, can be transferred to humans and, on the other hand, can replace the tedious and cost-intensive animal models. Still in the year 1991, over 2 million animals have been employed for animal experiments in the federal states of the former Western Germany alone.

One starting point of pharmacological/toxicological research which has recently grown more and more important is heart differentiation. From the stereotypically proceeding heart cell development, conclusions can be drawn to pathological and toxicological changes of cardiomyocytes. Thus, for example, it is known that the receptor state and the intracellular signal cascades are disturbed in cardiac hypertrophy (Yamazaki et al., J. Mol. Cell Cardiol. 27(1): 133–140 (1995)) and heart insufficiency (Johnson et al., Biochem. Pharmacol. 45(12): 2365–2372 (1993)). These pathologically altered cardiomyocytes are in part again similar to heart cells of early differentiation stages.

However, the examinations necessary for elucidating the properties of heart cells in early differentiation stages are technically difficult to perform with live animals and, if they can be performed at all, it is only in very complicated studies: On day 12–13, at the earliest, it is possible to prepare cardiomyocytes from a murine embryo, but such cells no longer correspond to an early cardiac differentiation stage. A detailed analysis of receptor expression during various differentiation stages requires a very high expense of animal material and is technically difficult to perform as set forth above. Similarly, the observation of the development of a relatively undifferentiated heart cell over several days or weeks is not possible with an animal model. In order to test the use of novel therapeutical agents, e.g., inotropic substances or antiarrhythmics or toxic substances, e.g., heavy metals or retinoids, an invasive monitoring of animals, e.g., swine, must be performed for weeks in animal experiments.

Now, it has been the object of the present invention to provide a cell culturing method which enables a simple characterization of the living cells and allows for functional examinations rather than being based on reporter genes such as Lac-Z (Niwa et al., 1991, Gene 108,193–199; Wobus et al., 1996, J. Cell Mol. Cardiol.; Metzger et al., 1996, Circ. Res., 78, 547–552), as with prior methods, the expression of which genes can be detected only after cell fixation and by means of a specific substrate.

Surprisingly, it has been found that ES cells can be stably transfected, using electroporation, with a DNA construct in which a gene coding for a non-cell-damaging fluorescent protein is coupled with a cell- and development-dependent promoter. This construct is integrated in the native DNA. After the specific activation of intracellular signals, the promoter is activated and the fluorescent protein expressed. Thus, ES cells which activate a cell-specific transcription factor at a certain point of differentiation could be recognized by their fluorescence emissions when being under fluorescent excitation.

Thus, the present invention relates to non-human mammal embryonic stem (ES) cells stably transfected with a DNA construct comprising
- a DNA sequence coding for a non-cell-damaging fluorescent protein; and
- a cell- and/or development-dependent promoter operably linked with said DNA sequence.

The ES cells are preferably derived from rodents, especially mice. Particularly preferred ES cells are D3 cells (Doetschmann et al., J. Embryol. Exp. Morphol. 87, 27 (1985)), R1 cells (Nagy et al., PNAS (1995)), E14 cells (Handyside et al., Roux Arch. Develop. Biol. 198, 48 (1989)), CCE cells (Bradley et al., Nature 309, 255 (1985)) and P19 cells (Mummery et al., Dev. Biol. 109, 402 (1985)).

As the "non-cell-damaging fluorescent protein" according to the present invention, there may be used the Green Fluorescent Protein (GFP) from the jellyfish *Auequorea victoria* (described in WO-A-95/07463, WO-A-96/27675 and WO-A-95/21191) and its derivatives "Blue GFP" (Heim et al., Curr. Biol. 6(2): 178–182 (1996)) and "Redshift GFP" (Muldoon et al.; Biotechniques 22(1): 162–167 (1997)). Preferred is the green fluorescent GFP, especially the GFP mutant contained in the deposited strain DSM 11633.

According to the present invention, the term "cell- and/or development-dependent promoter" is intended to mean a promoter which displays its promoter activity only in particular cell types and/or only in particular stages of cellular development, both in cell cultures (embryoid bodies) and in transgenic non-human mammals dervied from the ES cells according to the invention. In addition, any other known cell-specific promoter can be employed, e.g. for nerve cells, heart cells, neurons, glia cells, hematopoietic cells, endothelial cells, smooth muscle cells, skeletal muscle cells, cartilage cells, fibroblasts and epithelial cells.

In a preferred embodiment of the invention, the promoter is a promoter specific for heart cells. In particular, the following promoters may be mentioned: SMHC Minimal Promoter (specific for smooth muscle cells, Kallmeier et al., J. Biol. Chem. 270(52): 30949–30957 (1995)); Nkx-2.5 (specific for very early cardiomyocytes, Lints et al., Development, 119(2): 419–431 (1993)); human α-actin (specific for cardiac tissue, Sartorelli et al., Genes Dev., 4(10): 1811–1822 (1990)); MLC-2V (specific for ventricles, O'Brien et al., Proc. Natl. Acad. Sci. USA, 90(11): 5157–5161 (1993) and WO-A-96/16163).

In a preferred embodiment, the DNA construct includes further functional DNA sequences, especially enhancers and selective sequences. Such selective sequences include, e.g., neomycin and hygromycin.

The invention further relates to a method for preparing the ES cells according to the invention, comprising:
- introducing a DNA construct as defined above in starting ES cells of non-human mammals; and
- screening for stably transfected ES cells.

Said introducing may be effected by any method known to those skilled in the art. However, electroporation is preferred. The screening is preferably performed using the selective sequences present in the DNA construct.

The invention also relates to the above described DNA construct. Preferred constructs are the reporter constructs pCX-(β-act)GFP-Neo and pCX-(α-act)GFP-Neo (DSM 11633) as depicted in FIGS. 1 and 2.

The invention also relates to a cell culture exhibiting cell-type specific expression of a non-cell-damaging fluorescent protein, obtainable by culturing the ES cells according to the invention. In a preferred embodiment, the cells are in the form of aggregates (embryoid bodies). In the preparation of the embryoid body, standard methods are followed, e.g., the "hanging drop" method or methylcellulose culture (Wobus et al., Differentiation (1991) 48, 172–182).

These cell cultures can be used in methods for the toxicological examination of substances, e.g., retinoids, heavy metals and pharmaceutical agents. They have substantial advantages over any cell culture models used to date:
a) The living, unfixed cells can be observed while differentiating; thus, for example, the growth of the heart cells can be continuously observed in the beating area.
b) Cells in an early stage of development can be made accesible to electrophysiological and other measuring methods because, being fluorescent cells, they are easily discerned (see FIG. 3). This means an essential simplification of the functional study of these cells.
c) A single cell preparation implies a loss of cells. To visualize the small number of the cells still present, the cells expressing the fluorescent protein are advantageous. The method can be complemeted with a FACS sorting method whereby homogeneous cell populations can be obtained. Thus, it is also possible to perform studies (e.g., molecular-biological ones) with a larger population of phenotypically differentiated ES cells.
d) Since the ES cells expressing the fluorescent protein become visible in the EB upon activation of heart-specific promoters, the growth of the heart-related cells can be determined under pharmacological/toxicological conditions by a quite simple method. For routine examinations of the effect of different substances on heart cell differentiation, the area of cells expressing fluorescent protein in the EB could be determined at different times, and thus it could be established whether these substances quantitatively or qualitatively influence the differentiation of heart cells. For quantitatively more precise results, the cells could be dissociated and then subjected to the FACS sorting technique (FIG. 4).

Finally, the invention relates to a method for producing transgenic non-human mammals exhibiting cell-type specific expression of a non-cell-damaging fluorescent protein, comprising:
- injecting ES cells according to the invention into blastocysts of non-human mammals; and
- transferring the blastocysts into surrogate mothers;

transgenic non-human mammals obtainable by said method; and a method for examining stages of development of cells of non-human mammals, comprising the examination of the correspondingly marked cells of non-human mammals according to the invention using fluorimetric methods.

By the examination method according to the invention, an exact cell typing can be performed for the first time in vivo in the whole animal. Thus, fluorescent heart cells should be observed already in the early primordiums of the embryos, which would enable an in vivo observation of the development of the heart in the early embryonic stage. Also, the heart cells could be easily identified thereby in different stages of development.

The invention will be further illustrated by the following Figures and Examples.

Figure 3:
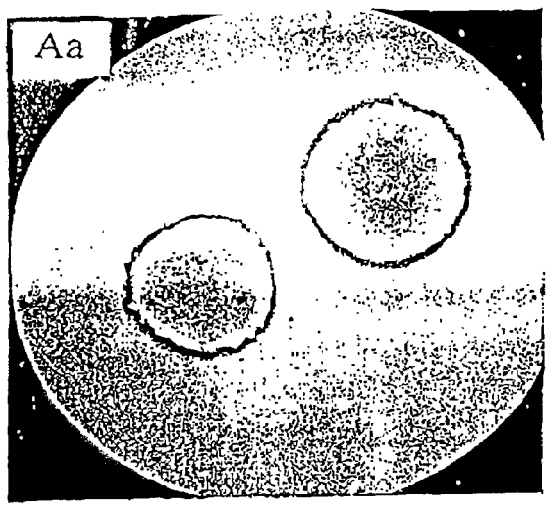
Figure 3:
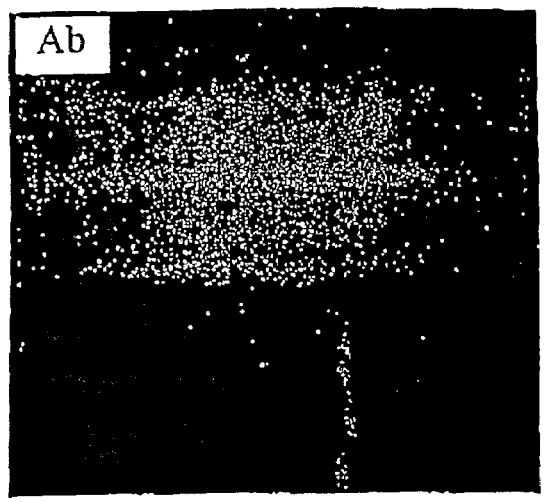
Figure 3:
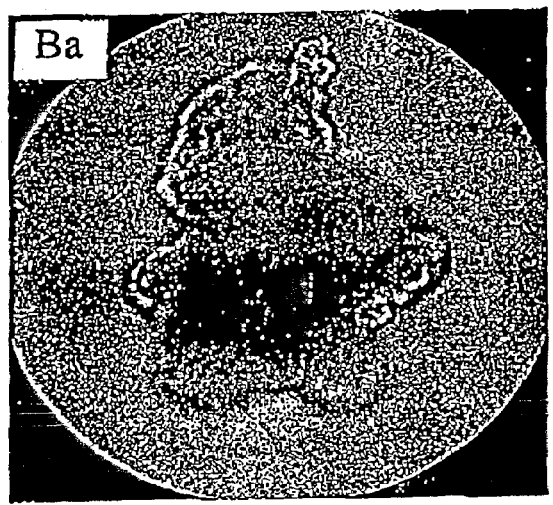
Figure 3:
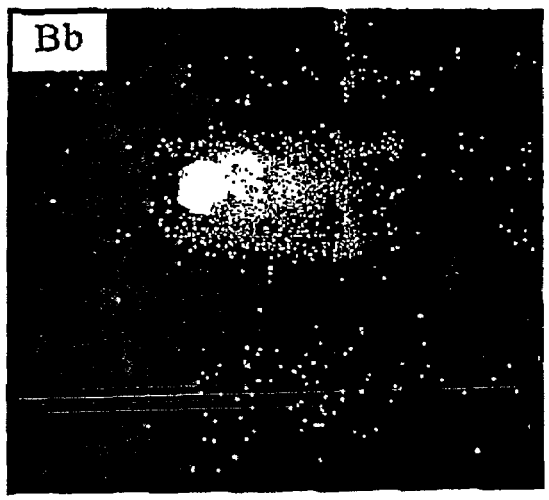
Figure 3:
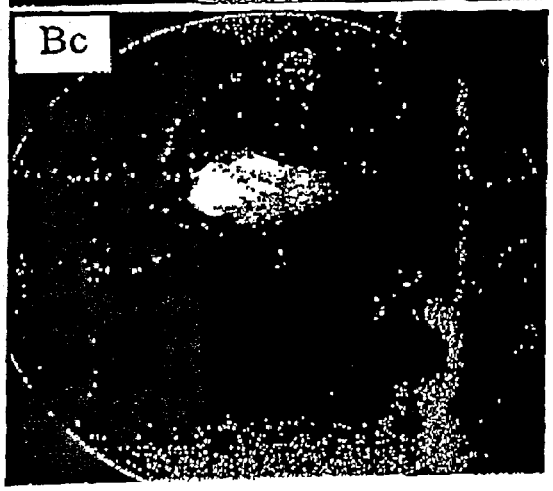

FIG. 3, Part A: Two young EBs are shown in suspension under transmitted light (Aa) and under 488 nm excitation (Ab). Since heart cells have not yet differentiated in these early EBs, a green fluorescence cannot be seen.

Part B: EB after 3 days of plating (7+3 days) under transmitted light (Ba), under 488 nm fluorescence excitation (Bb) and in a combination of transmitted light and 488 nm fluorescence excitation. In this EB, a relatively small spontaneously beating area could be observed. This corresponds to the portion of the EB exhibiting spontaneous contractions. The EBs were imaged with 20× magnification.

Figure 4:
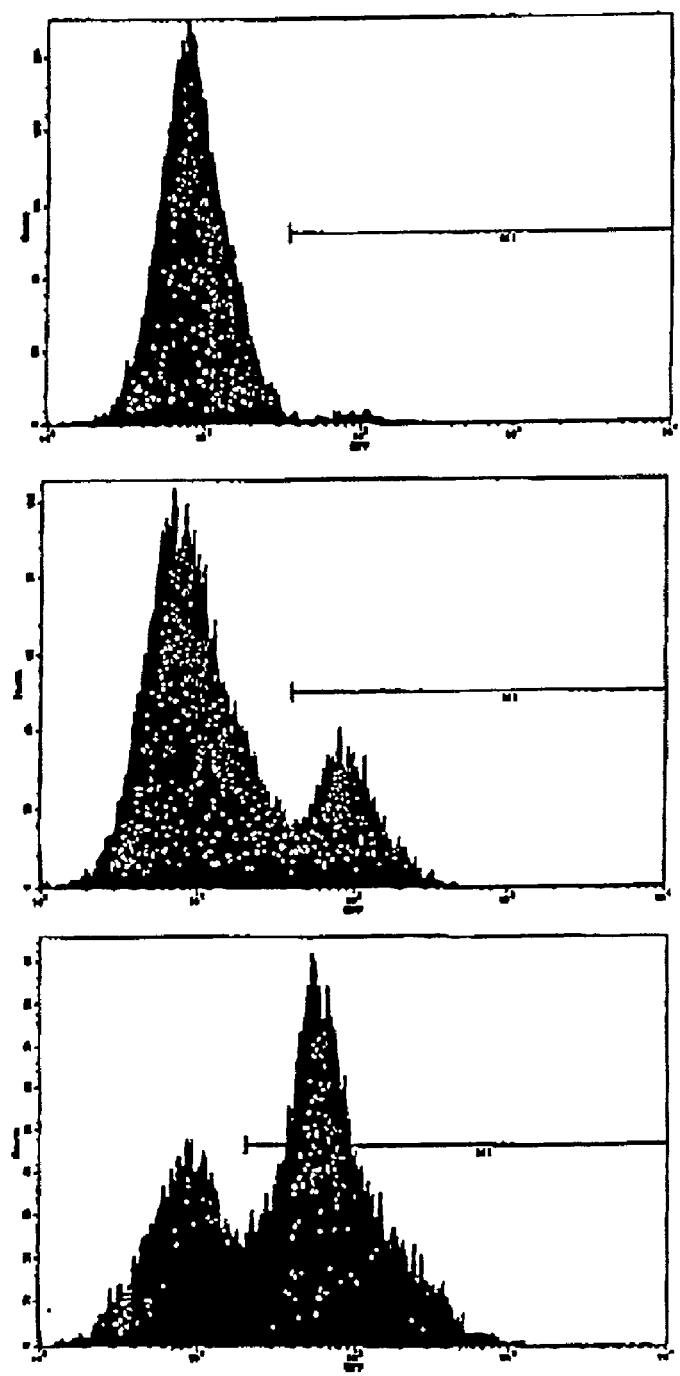

FIG. 4: FIG. 4 shows distribution histograms of cells from EBs established by the FACS method, obtained from ES cells with pCX-(α-act)GFP-Neo. The construct was linearized using AatI so that the CMV-IE enhancer was destroyed.
(a) ES cells
(b) after 2 days of suspension (2+2 days)
(c) 5 days after plating (7+5 days)

x axis: intensity of GFP fluorescence (FACS units), y axis: cell counts.

EXAMPLES

Example 1

Figure 1:
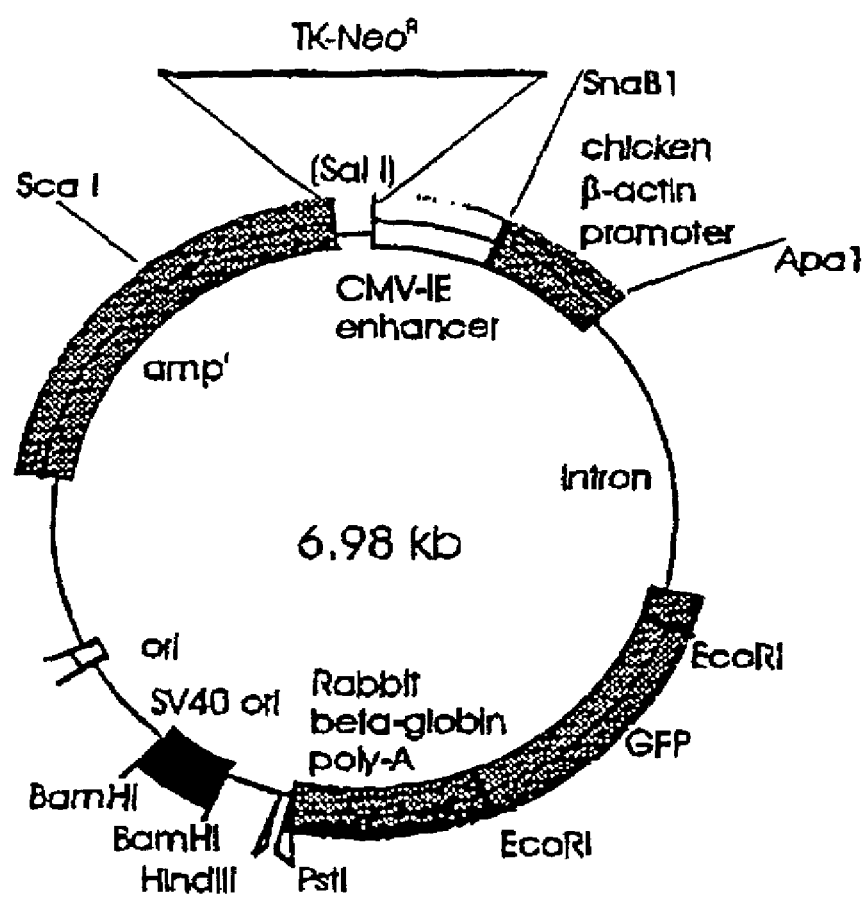
FIG. 1 shows the reporter gene construct pCX-(β-act) GFP-Neo used in Example 1.

Preparation of Stable ES Cell Lines Expressing GFP Under a Strong Ubiquitous Promoter, and Differentiation and Properties of Cardiomyocytes Derived from These Cells a) Preparation of the GFP Expression Construct: The pCX GFP expression vector supplied by Dr. Okabe (University of Osaka, Japan) which contains a GFP-coding sequence under a chicken α-actin promoter (M. Ikawa, K. Kominami, Y. Yoshimura, K. Tanaka, Y. Nishimune and M. Okabe, Develop. Growth Differ, (1995) 37, 455–459) was modified as follows:

A SalI-XbaI restriction fragment containing a neomycin (G418) resistance gene of pTL2Neo (supplied by Dr. Tarakhovsky) was inserted into the SalI site of pCX-GFP by ligation with blunt ends. The resulting construct pCX-(β-pact)GFP-Neo (FIG. 1) was used for the electroporation of D3 cells.

b) Electroporation and Selection Procedure: The pCX-(β-act)GFP-Neo construct was linearized with restrictase ScaI (outside the GFP expression cassette) and used for the electroporation of the D3 line of ES cells under the following conditions:

DNA: 20–40 μg, cells: 7×10/ml in 0.8 ml PBS buffer, electroporation cuvette BioRad 0.4 cm (Cat. No. 165-2088), electroporation apparatus BioRad (Gen Pulser), 240 V, 500 μF.

After the electroporation, the cell suspension was placed on ice for 20 min and then transferred to a 10 cm tissue grade Petri dish with a G418 resistance feeder layer in 10 ml of DMEM medium with 15% FCS (fetal calf serum). Two days later, 300 μg/ml neomycin (G418, Gibco) was added to select G418-resistant cells. The medium with G418 (300 μg/ml) was exchanged every other day. After 8 to 10 days of selection, drug-resistant colonies appeared which were tested for GFP expression by fluorescence microscopy.

About 95% of the G418-resistant colonies exhibited a strong GFP expression (green luminosity), indicating a high degree of activity of the β-actin promoter (β-actin is one of the main proteins of the cytoskeleton) in ES cells. The colonies were taken up by sucking with a Pasteur pipette, individually trypsinized and subsequently transferred to 48- and 24-well plates with feeder layers with G418 (300 μg/ml) for proliferation. Finally, several stable ES clones bearing 1 to 5 copies of the GPS gene under the control of the chicken β-actin promoter were detected and used for the production of embryoid bodies (EBs).

c) Differentiation and Analysis of the Cardiomyocytes: EBs were developed according to the standard "hanging drop" method (A. Wobus, G. Walluka and J. Hescheler; Differentiation (1991) 48, 173–182).

In all stages of development prior to plating, the EBs derived from ES cells having an integrated GFP expression vector under the control of the β-actin promoter exhibited an intense green luminosity under the fluorescence microscope. After plating, the GFP expression was distributed in unequal proportions among different cell types which appeared in the course of differentiation. The brightest green luminosity in EBs after the occurrence of contractile myocardiocytes coincides with corresponding beating regions rathr than beating core parts (central parts) of EBs.

Other regions of the EBs show different degrees of GFP expression from weak to strong which indicates the well-known wide-spread expression of β-actin as a main component of the cytoskeleton in various cell types.

These visual observations are confirmed by histograms of the distribution of GFP expression in the cell populations in the developing EBs, obtained by FACS analysis (flow cytofluorimetry). They show the left-hand shift and enlargement of initially sharp symmetrical peaks of the histogram, which indicates a transition from a high and relatively homogeneous GFP expression in a population of proliferating undifferentiated ES cells to a broad distribution of the same among the population of differentiating cell types.

EBs were differentiated using collagenase and plated onto slides and then cultured for 2–3 days after which electrophysiological measurements were made according to the standard procedure (V. Maltsev, A. Wobus, J. Rohwedei, M. Bader and 3. Hescheler, Circ. Res. (1994) 75(2), 233–244).

Isolated spontaneously beating cardiomyocytes which strongly express GFP have all the electrophysiological properties typical of cardiomyocytes including action potentials, $Ca^{2+}$, $Na^+$, $K^+$ and $I_f$ flows, which was shown by the patch-clamp technique.

Thus, stable ES cell lines which are strongly expressing GFP due to an expression vector integrated in the genome can differentiate into functionally mature contractile cardiomyocytes which have the same basic electrophysiological properties as cardiomyocytes which have differentiated from "normal" D3 cells.

Example 2

Figure 2:
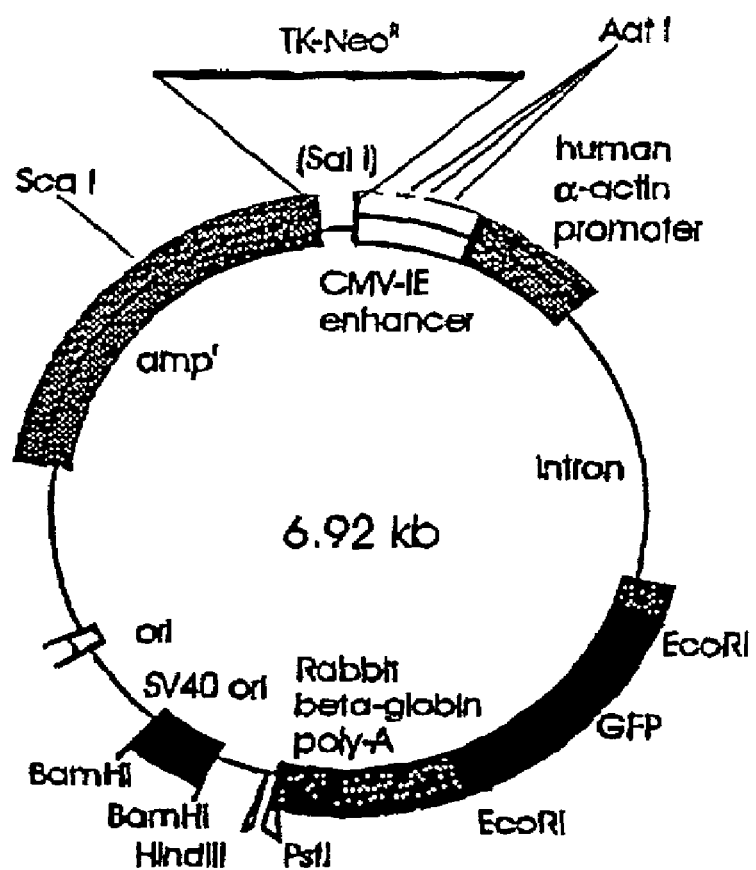
FIG. 2 shows the reporter gene construct pCX-(α-act) GFP-Neo (DSM 11633) used in Example 2.

Preparation of Stable ES Cell Lines Expressing GFP Under a Heart-Specific Promoter in Differentiating Cardiomyocytes a) Preparation of the GFP Expression Construct: From the plasmid pPv/B-Act-lacZ supplied by Dr. M. McBurney (University of Ottawa, Canada) which contained the segment (−440+6) of the heart-specific human α-actin promoter (A. Minti, L. Kedes; Molecular and Cellular Biology (1986) 6, 2125–2136; G. Pari, K. Jardine and M. McBurney; Molecular and Cellular Biology (1991) 11, 4796–4803), the promoter was excised using the restriction enzymes SalI and HindIII. In order to replace the chicken β-actin promoter by the heart-specific α-actin promoter, the pCX-GFP expression vector (see Example 1) was cleaved with the restrictases SnaBI and ApaI to excise the chicken β-actin promoter. Subsequently, the above mentioned SalI-HindIII fragment of the heart-specific α-actin promoter was inserted by ligation with blunt ends, The restrictases Tth111I, SalI and HinfI were used to select plasmid clones in which the heart-specific α-actin promoter had been inserted in the right orientation with respect to the GFP-coding sequence. A neomycin (G418) resistance gene as described in Example 1a) was then inserted in the SalI site, and the resulting plasmid pCX-(α-act)GFP-Neo (FIG. 2) was used for the electroporation of D3 cells.

b) Electroporation and Selection Procedure: The pCX-(α-act)GFP-Neo was linearized with ScaI (outside the GFP expression cassette, as described in Example 1b)) or AatI to destroy the cytomegalovirus (CMV-IE) enhancer (see below). The electroporation and the G418 selection procedure were performed as described in Example 1b).

c) Analysis of the Cell Population and GFP Expression Under the Control of the Heart-Specific α-Actin Promoter During the Differentiation of Cardiomyocytes: EBs were developed as described in Example 1c). In contrast to the above described patterns of GFP expression under the control of the β-actin promoter, ES cells bearing the pCX-(α-act)GFP-Neo integrated in the genome exhibit no or only a very weak signal which is visible by fluorescence microscopy. The FACS analysis shows that the average level of the green fluorescence of D3 cells containing pCX-(α-act)GFP-Neo linearized by SacI is about 35 to 40 times lower than for cell lines bearing pCX-(β-act)GFP-Neo. During the development of the EBs, a right-hand shift and enlargement of the initial peak of the GFP fluorescence histogram obtained by FACS was seen. The beating regions which occurred 2 to 4 days after plating the EBs show a green luminosity visible by fluorescence microscopy at a level comparable to that of the GFP expression in ES cells bearing pCX-(β-act)GFP-Neo. Perhaps, the beating regions consisting of functionally mature cardiomyocytes are merely regions having an intense visible luminosity among other cell types in developing EBs. By daily monitoring, it is possible to detect separated luminous regions 1 to 1.5 days before they start to beat.

The heart-specific character of GFP expression was confirmed by α-actin specific immunostaining of single cells, which correlates with the GFP expression under the control of the heart-specific a-actin promoter.

d) Preparation of ES Cell Lines Having a Low Initial Non-Specific Level of GFP Expression: The above mentioned ES clones with integrated pCX-(α-act)GFP-Neo showed unambiguous cardiomyocyte-specific expression patterns which resulted in an evident coincidence of luminous and beating regions. However, the initial level of the GFP expression of these undifferentiated cells which is 5 to 10 times higher than for a negative control (intact ES cells) could impede the detection of the cells in the very first stages of differentiation.

In order to lower the initial level of non-specific GFP expression, a number of new cell lines were generated using pCX-(α-act)GFP-Neo linearized with AatI restrictase (FIG. 2) to enable destruction of the CMV-IE enhancer.

The latter was present in the original expression vector, and it was assumed that this was the reason for the initial non-specific "background".

After electroporation and the selection procedure, the G418-resistant clones showed a much higher diversification of the initial GFP expression than was shown by clones with an intact CMV-IE enhancer. Several ES clones with the lowest "background" were selected by FACS screening. These clones have an about 5 times lower initial fluorescence intensity and may be comparable with cells of the negative control (wild type) without a GFP vector. After the preparation of EBs from corresponding ES cell clones, some of them showed GFP expression in differentiating cardiomyocytes which was detectable both by fluorescence microscopy and by FACS analysis. The FACS analysis exhibited a high resolution between cells having entered heart-specific differentiation and the remainder of the cell population which showed the pronounced one-to-two peak character of histogram dynamics during the EB development (FIG. 4).

Thus, the described approach allows to examine the differentiation of ES cells into cardiomyocytes "in vitro", the GFP expression vector with the heart-specific promoter being used as a "living" reporter gene system which renders cells in the early stages of development discernible.

The above described plasmid pCX-(α-act)GFP-Neo has been deposited on Jun. 27, 1997, with the Deutsche Sammlung von Mikroorganismen und Zellkulturen GmbH, Maschroder Weg 1b, D-38124 Braunschweig, under the designation of DSM 11633.

The invention claimed is:

1. A cell culture exhibiting cell-type specific or development-specific expression of a non-cell damaging fluorescent protein comprising embryoid bodies formed by aggregates of embryonic stem cells stably transfected with a DNA construct comprising:
   a) a DNA sequence coding for said non-cell damaging fluorescent protein; and
   b) a promoter, wherein said promoter is activated after differentiation of the stem cells;
   wherein said DNA construct is the plasmid pCX-(α-act) GFP-Neo (DSM 11633).

2. A cell culture exhibiting cell-type specific or development-specific expression of a non-cell damaging fluorescent protein comprising embryoid bodies formed by aggregates of embryonic stem cells stably transfected with a DNA construct comprising:
   a) a DNA sequence coding for said non-cell damaging fluorescent protein; and
   b) a promoter, wherein said promoter is substantially inactive in undifferentiated embryonic stem cells;
   wherein said DNA construct is the plasmid pCX-(α-act) GFP-Neo (DSM 11633).

3. A DNA construct comprising the plasmid pCX-(α-act) GFP-Neo (DSM 11633).

* * * * *